United States Patent
Bowman

(10) Patent No.: US 9,516,851 B2
(45) Date of Patent: Dec. 13, 2016

(54) ONION VARIETY NUN 03010 ON

(71) Applicant: Nunhems B.V., Nunhem (NL)

(72) Inventor: Michael Bowman, Bakersfield, CA (US)

(73) Assignee: NUNHEMS B.V. (NL)

( * ) Notice: Subject to any disclaimer, the term of this patent is extended or adjusted under 35 U.S.C. 154(b) by 786 days.

(21) Appl. No.: 13/782,033

(22) Filed: Mar. 1, 2013

(65) Prior Publication Data

US 2013/0180002 A1    Jul. 11, 2013

(51) Int. Cl.
*A01H 5/12* (2006.01)
*C12N 15/82* (2006.01)
*A01G 1/00* (2006.01)
*A01H 5/04* (2006.01)

(52) U.S. Cl.
CPC ............... *A01H 5/12* (2013.01); *A01G 1/001* (2013.01); *A01H 5/04* (2013.01); *C12N 15/8241* (2013.01)

(58) Field of Classification Search
None
See application file for complete search history.

(56) References Cited

PUBLICATIONS

Boyhan et al. (2007 Georgie Onion Research Extension Report).*

* cited by examiner

*Primary Examiner* — Brent Page
*Assistant Examiner* — Jared Shapiro

(57) ABSTRACT

The invention relates to the field of *Allium* in particular to a new variety of *Allium cepa* L. designated NUN 3010 ON plants, seeds and bulbs thereof as well as plant breeding methods involving NUN 3010 ON.

19 Claims, 1 Drawing Sheet

ONION VARIETY NUN 03010 ON

FIELD OF THE INVENTION

The present invention relates to the field of plant breeding and, more specifically, to the development of the short day onion variety NUN 3010 ON.

BACKGROUND OF THE INVENTION

Onions belong to the lily family, Amaryllidaceae, and the genus, *Allium*. Alliums comprise a group of perennial herbs having bulbous, onion-scented underground leaves, including such commonly cultivated crops as garlic, chives, and shallots. It also includes ornamental species grown for their flowers.

Onions are an important vegetable world-wide, ranking second among all vegetables in economic importance with an estimated value of $6 billion dollars annually. The onion is also one of the oldest cultivated vegetables in history. The common garden onions are in the species *Allium cepa*. Onions are classified in numerous ways, by basic use, flavor, color, shape of the bulb, and day length. Onions come in white, yellow, and red colors. The bulb may be rounded, flattened, or torpedo shaped.

Commercial onions include "storage onions", "fresh onions", "pearl or mini onions", and "green onions". "Fresh onions" tend to have a lighter color with a thin skin, a milder, sweeter flavor, and must be eaten fresh as they do not store well. These onions are available in red, yellow, and white colors.

Storage onions are available from harvest, which is at the beginning of August, and are stored and available throughout the winter months up to about March. Storage onions have a darker skin that is thicker than that of a fresh onion. They are also known for intense, pungent flavor, higher percentage of solids and desirable cooking characteristics. These onions are also available in red, yellow and white colors. Not all long day length type (long day type) onions are suitable for storage. A true storage onion is one that can be harvested in late summer or fall, and stored, under proper conditions, until the spring, when the fresh onion crop is again available.

"Spanish onion", "Spanish onions", or "Spanish type" are terms applied to various long-day onions, generally yellow, though some white, and generally varieties that are large and globe-shaped. Spanish onion is commonly applied to various long day type onions of the type grown in western states of the United States (California, Idaho, Oregon, Washington, Colorado) with a bulb size averaging 300-700 grams (g) (typically over 3 inches up to 4 inches but also up to 5 inches in diameter for bulbs classified as "colossal").

Onion varieties initiate bulbing when both the temperature and a minimum number of daylight hours reach certain levels. When onions are first planted, they initially develop their vegetative growth, with no sign of bulb formation until the proper day length for that onion variety triggers the signal to the plant to stop producing above ground vegetative growth and start forming a bulb. Onions are thus sensitive to the hours of daylight and darkness they receive, and for most varieties it is only when the specific combination of daylight and darkness is reached, that the bulb starts to form. Onions are therefore classified by the degree of day length that will initiate bulb formation. Onions are described as short-, intermediate-, and long-day length types. Short day means that bulbing will initiate at 11 to 12 hours of daylight. Intermediate day is used for onions bulbing at 12 to about 14 hours of daylight. Long day onions require about 14 or more hours of daylight for bulb formation to start.

Growers producing onions in more northerly climates plant long-day length onions. Daylight length varies greatly with latitude, and at higher latitudes long-day onions will produce sufficient top growth before the day length triggers bulbing to produce a large bulb. A short-day onion grown in the North (higher latitudes) will bulb too early and produce relatively small bulbs.

Short day onions are preferred for southern areas such as southern Texas, southern California and Mexico. If a long day type onion is planted in such a short day climate, it may never experience enough day length to trigger the bulbing process.

Onions are also classified on flavor, with the common designations of sweet, mild, and pungent. The flavor of the onion is a result of both the type of onion and the growing conditions. For instance, soils containing a high amount of sulfur result in more pungent flavored onions. Sweetness in onions is caused by the sugars glucose, fructose and sucrose. Onions also contain polymers of fructose called fructans. Onion cultivars differ quite markedly in the relative amounts of sucrose, glucose, fructose and fructans which they contain. They also differ in sugars according to length of storage and location in the bulb. Short day cultivars, which are poor storers, tend to have higher levels of sucrose, fructose and glucose, but hardly any of the fructans. In contrast, long day type cultivars and intermediate storage cultivars such as Pukekohe Longkeeper have less sucrose, glucose and fructose and higher amounts of fructans.

Short day varieties do not keep well in storage conditions, and the pungency of short day varieties can climb considerably during storage. Present production in North America and Europe allows harvest of short day onions from mild winter regions from November through April. Long day onions are available fresh in the late summer and as storage onions from September through March, or even year round, have not been available in low pungency varieties. Sweet onions must be imported from the southern hemisphere to fill the gap in sweet onion production (November-February). In the United States, regions like Georgia and Texas produce short day onions from March to June, while low pungency onions available from November to February are short day onions, produced in the southern hemisphere.

The use of a type of onion is depending on a customer's preference for taste, aroma, appearance and color of an onion. There is thus a need for new short day onions with new appearance and color properties.

SUMMARY OF THE INVENTION

In one aspect, the present invention provides an onion plant of the variety designated NUN 3010 ON (also referred to as "NUN 3010" herein), which is a short-day onion variety. Parts of the onion plant of the present invention are also provided, for example, including a leaf, pollen, an ovule, a bulb and a cell of the plant.

The invention also concerns seed of the hybrid onion variety NUN 3010 ON, i.e. seeds from which the variety NUN 3010 ON can be grown. The onion seed of the invention may be provided as an essentially homogeneous population of onion seed. Therefore, seed of the invention may be defined as forming at least about 97% of the total seed, including at least about 98%, 99% or more (100%) of the seed. The population of onion seed may be particularly defined as being essentially free from other seeds than those from which NUN3010 ON can be grown. The seed population may be separately grown to provide an essentially homogeneous population of onion plants according to the invention. Also encompassed are seeds grown from seeds of onion variety NUN 3010 and plant parts thereof such as a leaf, pollen, an ovule, a bulb and a cell.

Another aspect refers to an onion plant, or a part thereof, having "essentially all the physiological and morphological characteristics" of an onion plant of onion variety NUN 3010 or essentially all of the morphological and/or physiological characteristics except for one, two, three, four or five of the physiological and/or morphological characteristics of NUN 3010 ON. Such Essentially Derived Varieties (EDVs) can for example be generated by breeding with NUN 3010 ON or by identifying phenotypic variants of NUN 3010 ON.

Another aspect refers to phenotypic variants of NUN 3010, being derived from NUN 3010 by selection of a mutant or somaclonal variant or an off-type. Such a phenotypic variant of NUN3010 is an onion plant having all "distinguishing characteristics" of NUN3010, or an onion plant having all distinguishing characteristics and also one, two or three "further distinguishing characteristics" of NUN 3010. Such a phenotypic variant of NUN 3010 may, thus, differ from NUN 3010 in morphological and/or physiological characteristics of Table 1, but retains the distinguishing (and optionally one or more of the further distinguishing characteristics) of NUN 3010. The phenotypic variant of NUN 3010 may be a somaclonal variant, a mutant or an off-type. However, the variant phenotype is preferably genetically stable, also in the mature plants regenerated from the cell or tissue culture. That means, the phenotypic variant does not show variation in phenotype which are transient and are not genetically stable.

In another aspect of the invention, a cell- or tissue culture of regenerable cells of a plant of variety NUN 3010 is provided, or of a phenotypic variant of NUN 3010 or of an EDV of NUN3010. The cell- or tissue culture will preferably be capable of regenerating plants capable of expressing all of the physiological and morphological characteristics of a plant of the invention as shown in Table 1, or of the phenotypic variant of NUN3010 or of an EDV of NUN3010, and of regenerating plants having substantially the same genotype as the plants from which the cells or tissues were obtained. The regenerable cells in such cell- or tissue cultures may be derived, for example, from bulbs or bulb parts (e.g. scales), sheath, embryos, meristems, cotyledon, pollen, ovaries, leaves, anthers, roots, root tips, pistil, flower, seed and stalk of NUN 3010 or of a phenotypic variant or an EDV of NUN 3010. Thus, a cell- or tissue culture may comprise regenerable cells from bulbs, sheath, embryos, meristems, cotyledon, pollen, ovaries, leaves, anthers, roots, root tips, pistil, flower, seed and stalk. Still further, the present invention provides onion plants regenerated from a cell- or tissue culture of the invention, the plants having all the physiological and morphological characteristics of a plant of the invention when grown under the same conditions.

In a further aspect the cell- or tissue culture can be used to select phenotypic variants, such as a mutant or somaclonal variant, of NUN 3010. Such phenotypic variants are also an embodiment of the invention. These phenotypic variants may comprise essentially all morphological and/or physiological characteristics of NUN 3010, except 1, 2, 3, 4, or 5; or they may comprise all distinguishing characteristics of NUN 3010 and optionally also one, two or three of the further distinguishing characteristics of NUN 3010, but may statistically significantly differ from NUN 3010 in one or more of the other characteristics listed in Table 1.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots to obtain rooted plantlets. In some of these embodiments, the method further comprises growing plants from said rooted plantlets.

In yet another aspect of the invention, processes are provided for producing onion seeds, plants and bulbs, which processes generally comprise crossing a first parent onion plant with a second parent onion plant, wherein at least one of the first or second parent onion plants is a plant of the variety designated NUN 3010.

These processes may be further exemplified as processes for preparing hybrid onion seed or plants, wherein a first onion plant is crossed with a second onion plant of a different, distinct variety or line (e.g. an inbred line) to provide a hybrid that has, as one of its parents, the onion plant variety NUN 3010. In one aspect, NUN 3010 is the male parent, while another onion line or variety is the female parent.

In another embodiment of the invention, onion variety NUN 3010 is crossed to a second onion plant to produce hybrid (F1) seed. In any cross herein, NUN3010 may be the male or female parent. In these processes, crossing will result in the production of seed. The seed production occurs regardless of whether the seed is collected or not. The F1 seeds are an embodiment of the invention, as are onion plants grown from these F1 seeds, and parts thereof, such as harvested bulbs.

In another embodiment of the invention, onion variety NUN 3010 ON is selfed, to produce S1, S2, S3, or further generation, progeny seeds on NUN 3010 plants. The S1, S2, S3, S4, or further generation, seeds are an embodiment of the invention, as are onion plants grown from these seeds, and parts thereof, such as harvested bulbs.

In one embodiment of the invention, the first step in "crossing" comprises planting seeds of a first and a second parent onion plant, often in proximity so that pollination will occur for example, mediated by insect vectors. Alternatively, pollen can be transferred manually.

A second step may comprise cultivating or growing the seeds of the first and the second parent onion plants into plants that bear flowers. A third step may comprise preventing self-pollination of the plants, such as by emasculating the male portions of flowers, (e.g., treating or manipulating the flowers to produce an emasculated parent onion plant). Male-sterility systems may also be used in onions for the same purpose. Male sterile plants will not produce viable pollen and can be pollinated by plants of another onion line or variety. Thereby essentially 100% hybrid seeds are produced on the male sterile plant.

The present invention also provides the onion seeds and plants produced by a process that comprises crossing a first parent onion plant with a second parent onion plant, wherein at least one of the first or second parent onion plants is a plant provided herein, such as variety NUN 3010 or a phenotypic variant or EDV of NUN 3010. In another embodiment of the invention, onion seed and plants produced by the process are first filial generation (F1) hybrid onion seed and plants produced by crossing a plant in accordance with the invention with another, distinct plant, such as another inbred onion line. The present invention further contemplates plant parts (e.g. bulbs) of such an F1 hybrid onion plant, and methods of use thereof. Therefore, certain exemplary embodiments of the invention provide an F1 hybrid onion plant and seed thereof.

In still yet another aspect, the present invention provides a method of producing a plant or a seed derived from variety NUN 3010, the method comprising the steps of: (a) obtaining a (F1) progeny onion plant derived from said variety by crossing a plant of variety NUN 3010 (or a selfing thereof, e.g. S1) with a second onion plant (of *A. cepa* or other *Allium* species); and (b) selfing the F1 progeny plant one or more times (to produce an F2, F3, etc.) or crossing it or the F1, F2, etc. to the second onion plant or to a third onion plant (of *A. cepa* or other *Allium* species) to produce a seed of a progeny plant of a subsequent generation. Alternatively, step (b) may comprise crossing the F1 progeny plant back to NUN 3010 (or the selfing of NUN3010), or selfing the F1 progeny plant one or more times and crossing the further selfed progeny plant (F2, F3, F4, etc.) back to NUN 3010 (or the selfing of NUN3010) to produce a seed of a progeny plant of a subsequent generation.

The method may additionally comprise: (c) growing a progeny plant of a further subsequent generation from said seed of a progeny plant of a subsequent generation and selfing the progeny plant of a subsequent generation or crossing it to the second, the third, or a further plant or to NUN3010; and repeating the steps for 3 or more times, e.g., an additional 3-10 generations to produce a further plant derived from the aforementioned starting variety. The further plant derived from variety NUN 3010 may be an inbred line or variety, and the aforementioned repeated crossing steps may be defined as comprising sufficient inbreeding to produce the inbred line or variety. In the method, it may be desirable to select particular plants resulting from step (b) and/or (c) for continued crossing according to steps (b) and (c). By selecting plants having one or more desirable traits, a plant is obtained which possesses some of the desirable traits of the starting plant as well as potentially other selected traits. Thus, either an EDV can be generated, i.e. an onion plant having all the morphological and/or physiological characteristics of NUN3010 and one, two or three, additional traits or characteristics or an onion plant having all the morphological and/or physiological characteristics of NUN3010 except for one, two, three, four, or five characteristics which may be changed, so that the plant differs significantly from NUN3010 in those one, two, three, four, or five characteristics.

One aspect of the invention refers to a method of producing an onion plant comprising crossing an onion plant of variety NUN 3010 with a second onion plant one or more times. This method comprises in one embodiment selecting progeny from said crossing.

In another aspect of the invention, an onion plant of variety NUN 3010 comprising an added heritable trait is provided, e.g., NUN3010 with an additional trait or an Essentially Derived Variety of NUN 3010 having one, two or three physiological and/or morphological characteristics which are different from those of NUN 3010 and which otherwise has all the physiological and morphological characteristics of NUN 3010, wherein a representative sample of seed of variety NUN 3010 has been deposited under NCIMB/ATCC Accession Number 42662. The heritable trait may comprise a genetic locus that is, for example, a dominant or recessive allele. In one embodiment of the invention, a plant of the invention is defined as comprising a single locus conversion. For example, one, two, three or more heritable traits may be introgressed at any particular locus using a different allele that confers the new trait or traits of interest. In specific embodiments of the invention, the single locus conversion confers one or more traits such as, for example, herbicide tolerance, insect resistance, disease resistance and modulation of plant metabolism and metabolite profiles. In further embodiments, the trait may be conferred by a naturally occurring gene introduced into the genome of the variety by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location. Thus, the invention comprises a method of producing a plant comprising an added desired trait, the method comprising introducing a transgene conferring the desired trait into a plant of onion variety NUN 3010.

For example, in certain embodiments, the invention provides methods of introducing a desired trait into a plant of the invention comprising: (a) crossing a plant of variety NUN 3010 (or a selfing thereof) with a second onion plant (e.g. *A. cepa* or another *Allium* species) that comprises a desired trait to produce F1 progeny and optionally selfing the F1 one or more times to produce F2 or F3, etc. progeny, (b) selecting an F1 progeny or F2 or F3, etc. progeny that comprises the desired trait(s), e.g., one, two, three or more desired trait(s), (c) crossing the selected F1 or F2 or F3 or F4, etc. progeny with a plant of variety NUN 3010 to produce backcross progeny, optionally selfing the backcross progeny, and (d) selecting backcross progeny (or selfed backcross progeny) comprising the desired trait(s) and which otherwise has all the physiological and morphological characteristics of variety NUN 3010. Optionally, steps (c) and (d) can be repeated one or more times, e.g., three or more times such as three, four, five, six or seven times, in succession to produce selected fourth, fifth, sixth, seventh or eighth or higher backcross progeny that comprises the desired trait. The invention also provides onion plants produced by these methods, i.e. plants having all the morphological and/or physiological characteristics of NUN3010 and one, two or three, additional traits or characteristics.

Still yet another aspect of the invention refers to the genetic complement of an onion plant variety of the invention. The phrase "genetic complement" is used to refer to the aggregate of nucleotide sequences, the expression of which defines the phenotype of, in the present case, an onion plant of, or a cell or tissue of that plant. A genetic complement thus represents the genetic makeup of a cell, tissue or plant, and a hybrid genetic complement represents the genetic make-up of a hybrid cell, tissue or plant. The invention thus provides onion plant cells that have a genetic complement in accordance with the onion plant cells disclosed herein, and plants, seeds and plants containing such cells.

Plant genetic complements may be assessed by genetic marker profiles, and by the expression of phenotypic traits that are characteristic of the expression of the genetic complement, e.g., gene expression profiles, gene product expression profiles and isozyme typing profiles. It is understood that a plant of the invention or a first generation progeny thereof could be identified by any of the many well-known techniques such as, for example, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (see, e.g., EP 534 858), and Single Nucleotide Polymorphisms (SNPs).

In still yet another aspect, the present invention provides hybrid genetic complements, as represented by onion plant cells, tissues, plants, and seeds, formed by the combination of a haploid genetic complement of an onion plant of the invention with a haploid genetic complement of a second onion plant, preferably, another, distinct onion plant. In another aspect, the present invention provides an onion plant regenerated from a tissue culture that comprises a hybrid genetic complement of this invention.

In still yet another aspect, the invention provides a method of determining the genotype of a plant of the invention comprising detecting in the genome of the plant at least a first polymorphism. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

In one embodiment of the invention, the invention provides a method for producing a seed of a variety derived from NUN 3010 comprising the steps of (a) crossing an onion plant of variety NUN 3010 with a second onion plant; and (b) allowing seed of a variety NUN 3010-derived onion plant to form. This method can further comprise steps of (c) crossing a plant grown from said variety NUN 3010-derived onion seed with itself or a second onion plant to yield additional variety NUN 3010-derived onion seed; (d) growing said additional variety NUN 3010-derived onion seed of step (c) to yield additional variety NUN 3010-derived onion plants; and optionally (e) repeating the crossing and growing steps of (c) and (d) to generate further variety NUN 3010-derived onion plants. For example, the second onion plant is of an inbred onion variety or line.

In certain embodiments, the present invention provides a method of producing onions comprising: (a) obtaining a plant of the invention, wherein the plant has been cultivated to maturity, and (b) collecting an onion bulb from said plant.

The invention also provides for a food or feed product comprising or consisting of a plant part described herein, preferably an onion bulb or part thereof, and/or an extract from a plant part described herein. The food or feed product may be fresh (e.g. comprising or consisting of whole or sliced or diced onion bulbs) or processed, e.g., canned, steamed, boiled, fried, blanched and/or frozen, etc.

Any embodiment discussed herein with respect to one aspect of the invention applies to other aspects of the invention as well, unless specifically noted.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DEFINITIONS

In the description and tables herein, a number of terms are used. In order to provide a clear and consistent understanding of the specification and claims, the following definitions are provided:

The term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and to "and/or."

When used in conjunction with the word "comprising" or other open language in the claims, the words "a" and "an" denote "one or more" unless specifically noted.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. The terms mentioned above also comprise the term "contain" which is limited to specific embodiments. Thus, one embodiment of the invention, when the terms "comprise," "have" and "include" are used to describe a plant, part thereof or a process, refers to an embodiment wherein the limiting term "contain" is used.

As used herein, "onion plant" or "onion" is a plant of genus *Allium* or a part thereof (e.g. a bulb). Onion includes all kinds of onions, such as short-day, intermediate-day and long-day onions according to bulb initiation in response to various lengths of daylight. Generally, a "short-day" length type onion plant (short-day, or SD, onion) responds to 11 to 12 hours of daylight for the initiation of bulb formation; an "intermediate-day" length type onion plant (intermediate-day, or ID, onion) needs 12 to 14 hours of daylight; and a "long-day" length type onion plant (long-day, or LD onion) requires about 14 or more contiguous hours of daylight for bulb formation to start. Onion includes, e.g., *Allium aggregatum* (e.g., chalottes and potato onion), *Allium cepa* and *Allium fistulosum*, and hybrids such as *Allium×proliferum, Allium×wakegi*, and the triploid onion *Allium×cornutum*. *Allium cepa* L. (common onion) is a cool season (tolerant of frost) biennial plant. By "biennial plant" it is meant that *Allium cepa* L. produces a bulb in the first season and seeds in the second. Onion plants may be grown at any temperature that allows for the growth and development of the plant. Generally herein "onion" or "onion plant" preferably refers to cultivated onion, *Allium cepa*, but in certain embodiments it refers to *Allium cepa* or another *Allium* species which can crossed with *Allium cepa* to produce viable offspring.

"Cultivated onion" or "*Allium cepa*" refers to plants of *Allium cepa*, i.e. varieties, breeding lines or cultivars of the species *Allium cepa*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

"USDA descriptors" are the plant variety descriptors described for onion in the "Objective description of Variety Onion *Allium cepa* L.", ST-470-16 (as published by U.S. Department of Agriculture, Agricultural Marketing Service, Science and Technology, Plant Variety Protection Office, Beltsville, Md. 20705 (available on the world wide web at www.ams.usda.gov/AMSv1.0/) and which can be downloaded from the world wide web at http://www.ams.usda.gov/AMSv1.0/getfile?dDocName=STELDEV3003776.

"UPOV descriptors" are the plant variety descriptors described for onion in the "Guidelines for the Conduct of Tests for Distinctness, Uniformity and Stability, TG/46/7 (Geneva 2009), as published by UPOV (International Union for the Protection of New Varieties and Plants, available on the world wide web at upov.int) and which can be downloaded from the world wide web at http://www.upov.int/edocs/tgdocs/en/tg046.pdf and is herein incorporated by reference in its entirety.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007 (The Royal Horticultural Society, charity No: 222879, PO Box 313 London SW1P2PE; sold by, e.g., TORSO-VERLAG, Obere Grüben 8•D-97877 Wertheim, Article-No.: Art62-00008 EAN-Nr.: 4250193402112).

"Genotype" refers to the genetic composition of a cell or organism.

"Phenotype" refers to the detectable characteristics of a cell or organism, which characteristics are the manifestation of gene expression.

As used herein, the term "plant" includes the whole plant or any parts or derivatives thereof, preferably having the same genetic makeup as the plant from which it is obtained, such as plant organs (e.g. harvested or non-harvested onion bulbs, leaves etc.), plant cells, plant protoplasts, plant cell and/or tissue cultures from which whole plants can be regenerated, plant calli, plant cell clumps, plant transplants, seedlings, mesocotyl, cotyledon, plant cells that are intact in plants, plant clones or micropropagations, or parts of plants (e.g. harvested tissues or organs), such as plant cuttings, vegetative propagations, embryos, pollen, ovules, flowers, anthers, leaves, seeds, bulbs, bulb-scales, (immature) flowers, clonally propagated plants, roots, stems, root tips, grafts, parts of any of these and the like. Also any developmental stage is included, such as seedlings, cuttings prior or after rooting, mature plants or leaves.

By "bulb" or "onion bulb" is meant the (commercially) (harvested when mature) edible portion of the onion plant. An onion bulb comprises an apex and concentric, enlarged fleshy leaf bases, also called fleshy scale leaves (see, e.g., FIG. 1). Onion bulbs may be developing (immature) onion bulbs or mature onion bulbs.

"Harvested plant material" refers herein to plant parts (e.g. a bulb detached from parts of the plant (such as leaves) or the rest of the plant) which have been collected for further storage and/or further use.

"Maturity" refers to the development stage of an onion bulb when said onion bulb has fully developed (reached its final size). In particular embodiments "maturity" is defined as the mature state of bulb development and optimal time for harvest. Typically, maturity of a bulb is reached when the vegetative phase of an onion plant is over and leaves and neck of the onion plant dry out.

As used herein, a "mature onion bulb" refers to any onion bulb that is ready for harvest. Generally, when 25-50% of the onion leaf tops have fallen over, the onion is ready for harvest.

"Harvested seeds" refers to seeds harvested from a line or variety, e.g. produced after self-fertilization or cross-fertilization and collected.

A plant having "essentially all the physiological and morphological characteristics" of NUN 3010 means a plant having all the physiological and morphological characteristics listed in Table 1 when grown under the same environmental conditions of the plant of NUN 3010 from which it was derived, e.g. the progenitor plant, the parent, the recurrent parent, the plant used for tissue- or cell culture, etc. The skilled person will understand that a comparison between onion varieties should occur when said varieties are grown under the same environmental conditions. For example, the plant may have all characteristics mentioned in Table 1 when grown under the conditions of the field trial described in this application. In certain embodiments, the plant having "essentially all the physiological and morphological characteristics of NUN 3010, except one, two, three, four or five characteristics" means that the onion plant, when grown under the same environmental conditions, (statistically) significantly differs from NUN 3010 in 1, 2, 3, 4 or 5 characteristics listed in Table 1, but does not differ (statistically) significantly in the other morphological and/or physiological characteristics of NUN 3010 listed in Table 1. So, the plant may have all characteristics mentioned in Table 1, except for one, two or three characteristics of Table 1, in which the plant may thus differ.

"Distinguishing characteristics" or "distinguishing morphological and/or physiological characteristics" refers herein the characteristics which are distinguishing between NUN 3010 and other short day onion varieties, such as variety Mata Hari, when grown under the same environmental conditions, especially the following (average) characteristics: 1) bulb size, 2) bulb weight, 3) bulb height, 4) bulb diameter and 5) sheath length. In one aspect the distinguishing characteristics further include at least one, two or all three of the following characteristics: 6) Bulb skin color 7) bulb interior color and 8) days to maturity. Thus, an onion plant "comprising the distinguishing characteristics of NUN 3010", refers herein to a onion plant which does not differ significantly from NUN 3010 in characteristics 1) to 5) above. In a further aspect the onion plant further does not differ significantly from NUN 3010 in at least one, two or all three characteristics selected from characteristics 6) to 8) above (also referred to as "further distinguishing characteristics").

The terms "phenotypic variant of NUN 3010", "phenotypic variant of onion plant designated NUN 3010", "variant of NUN 3010" refer to an onion plant, line or variety of onion which (statistically significantly) differs from NUN 3010 in one, two or three or more physiological and/or morphological characteristics when grown under the same conditions, but which comprises the distinguishing characteristics 1) to 5) above (and optionally also one or more of characteristics 6) to 8) above) of NUN 3010 when grown under the same conditions (i.e. which does not differ significantly from NUN 3010 in these characteristics). In one aspect the variant of NUN 3010 is derived from cells or tissues of NUN3010, representative seed of which having been deposited under Accession Number NCIMB 42662.

The physiological and/or morphological characteristics mentioned above are commonly evaluated at significance levels of 1%, 5%, 8% or 10% significance level, when measured under the same environmental conditions. For example, a progeny plant of NUN 3010 may have one or more (or all, or all except one, two or three) of the essential physiological and/or morphological characteristics of NUN 3010 listed in Table 1, or one or more or all (or all except one, two or three) of the distinguishing characteristics of NUN 3010 listed in Table 1 and above, as determined at the 1% or 5% significance level when grown under the same environmental conditions.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

The terms "gene converted" or "conversion plant" in this context refer to onion plants which are often developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are often developed by plant breeding techniques comprising or consisting of backcrossing, wherein essentially all of the desired morphological and physiological characteristics of an onion variety are recovered in addition to the characteristics of the single locus having been transferred into the variety via, e.g., the backcrossing technique and/or by genetic transformation. Likewise, a double loci converted plant/a triple loci converted plant refers to plants having essentially all of the desired morphological and physiological characteristics of given variety, expect that at two or three loci, respectively, it contains the genetic material (e.g., an allele) from a different variety.

A line or variety is referred to as an "Essentially Derived Variety" (EDV) i.e., shall be deemed to be essentially derived from another variety, "the initial variety" when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, or an off-type, the selection of a variant individual from plants of the initial variety, or transformation by genetic engineering or by further breeding with the initial variety and selecting a variant. Such a variant may be selected at any time, e.g. in the field or greenhouse, during breeding, during or after in vitro culture of cells or tissues, during regeneration of plants, etc. The term EDV, thus, also encompassed a "phenotypic variant" derived from NUN 3010 seed, plant tissue or cells.

"Plant line" is for example a breeding line which can be used to develop one or more varieties.

"Hybrid variety" or "F1 hybrid" refers to the seeds of the first generation progeny of the cross of two non-isogenic plants. For example, the female parent is pollinated with pollen of the male parent to produce hybrid (F1) seeds on the female parent.

"Progeny" as used herein refers to plants derived from a plant designated NUN 3010. Progeny may be derived by regeneration of cell culture or tissue culture or parts of a plant designated NUN 3010 or selfing of a plant designated NUN 3010 or by producing seeds of a plant designated NUN 3010. In further embodiments, progeny may also encompass plants derived from crossing of at least one plant designated NUN 3010 with another onion plant of the same or another variety or (breeding) line, or with a wild onion plant, backcrossing, inserting of a locus into a plant or selecting a plant comprising a mutation or selecting a variant. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Especially progeny of NUN 3010 which are EDVs or which retain all (or all except 1, 2 or 3) physiological and/or morphological characteristics of NUN 3010 listed in Table 1, or which retain all (or all except 1, 2, or 3) of the distinguishing characteristics and/or of the further distinguishing characteristics of NUN 3010 described elsewhere herein and in Table 1, are encompassed herein.

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one onion line or variety to another.

"Crossing" or "cross-pollination" refers to the fertilization by the union of two gametes from two parent plants, generally two different plants "Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Selfing" refers to self-pollination of a plant, i.e., the transfer of pollen from the anther to the stigma of the same plant.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) a bulb or part thereof, leaf, pollen, embryo, cotyledon, hypocotyl, cells, protoplasts, meristematic cell, root, root tip, pistil, anther, flower, shoot tip, shoot, stem, petiole, etc. When a whole plant is regenerated by vegetative propagation, it is also referred to as a vegetative propagation.

"Locus" (plural loci) refers to the specific location of a gene or DNA sequence on a chromosome. A locus may confer a specific trait.

"Linkage" refers to a phenomenon wherein alleles on the same chromosome tend to segregate together more often than expected by chance if their transmission was independent.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

As used herein, the terms "resistance" and "tolerance" are used interchangeably to describe plants that show no or significantly reduced symptoms to a specified biotic pest, pathogen, abiotic influence or environmental condition. These terms are also used to describe plants showing some symptoms but that are still able to produce marketable product with an acceptable yield. "Tissue Culture" refers to a composition comprising isolated cells of the same or a different type or a collection of such cells organized into parts of a plant. "Cell culture" refers to a composition comprising isolated cells of the same or a different type or a collection of such cells, where the cells are not organized into parts.

"Transgene" or "chimeric gene" refers to a genetic locus comprising a DNA sequence which has been introduced into the genome of an onion plant by transformation. A plant comprising a transgene stably integrated into its genome is referred to as "transgenic plant".

"Haploid" refers to a cell or organism having one set of the two sets of chromosomes in a diploid.

"Diploid" refers to a cell or organism having two sets of chromosomes.

"Polyploid" refers to a cell or organism having three or more complete sets of chromosomes.

"Triploid" refers to a cell or organism having three sets of chromosomes.

"Tetraploid" refers to a cell or organism having four sets of chromosomes.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for onion described herein. The mean, if not indicated otherwise within this application, refers to the arithmetic mean of measurements on at least 10 different, randomly selected plants of a variety or line.

Substantially equivalent" or "not significantly different" refers to a characteristic that, when compared, does not show a statistically significant difference (e.g., $p \geq 0.05$ using ANOVA) from the mean. Vice versa, "significantly different" or "statistically significantly different" refers to a characteristic that, when compared, does show a statistically significant difference (e.g., $p<0.05$ using ANOVA) from the mean.

DRAWINGS

The drawings described herein are for illustration purposes only and are not intended to limit the scope of the present teachings in any way.

FIG. 1 shows a comparison of typical onion bulbs of NUN 3010 and MATA HARI. In a field trial near Bakersfield (Calif., USA), the bulb weight of NUN 3010 was higher than bulb weight of MATA HARI, furthermore, the varieties differed in their bulb shape (NUN 3010 being more "top" shaped (USDA's Top Shape (Texas Grano 502; UPOV's Broad Obovate) and bulbs of MATA HARI being more "deep globe" (USDA's Deep Globe, UPOV's Rhombic) and bulbs of NUN 3010 had a noticeably lighter "rosier" bulb skin color than MATA HARI.

DETAILED DESCRIPTION OF THE INVENTION

The invention provides methods and compositions relating to plants, plant parts, seeds and progenies of onion variety NUN 3010. Variety NUN 3010 is most similar to the commercially available variety Mata Hari.

However, NUN 3010 differs from Mata Hari in one or more, e.g., at least two, at least three, optionally all morphological and/or physiological characteristics listed in the following (herein referred to as distinguishing characteristics; see also Table 1), when grown under the same environmental conditions:

1) average bulb size (USDA descriptor 6. BULBS); NUN 3010 has a significantly larger bulb size compared to MATA HARI; NUN3010 has a size of 3 (large) while Mata Hari has a size of 2 (medium).
2) average bulb weight (USDA descriptor 6. BULBS): NUN 3010 has a bulb weight which is significantly higher than that of Mata Hari; Nun3010 has a bulb weight that is at least 15%, 20% or 25% higher bulb weight than that of Mata Hari; in one aspect NUN3010 has an average bulb weight of at least 200 g, preferably at least about 220 g, 230 g or 240 g.
3) average bulb height: NUN3010 has an average bulb height which is significantly larger than the average bulb height of Mata Hari; in one aspect NUN3010 has a bulb height of at least about 7 cm, preferably at least about 7.2 cm, 7.3 cm, 7.4 cm or 7.5 cm.
4) average bulb diameter (USDA descriptor 6. BULBS): NUN 3010 has an average bulb diameter which is significantly larger than that of Mata Hari. Nun 3010 has an at least 10% or 15% larger bulb diameter compared to Mata Hari. In one aspect NUN3010 has a bulb diameter of at least about 7.5 cm, preferably at least about 7.8 cm, 8.0 cm, 8.3 cm, 8.4 cm, or 8.5 cm.
5) average sheath length (USDA descriptor 4. SHEATH). NUN 3010 has a sheath length which significantly shorter than that of Mata Hari. In one aspect the sheath length of NUN3010 is at least 15%, 20% or 25% shorter than that of MATA HARI. In one aspect the sheath length of NUN3010 is less than 50 mm, less than 48 mm, less than 47 mm or less than 46 mm.

Other morphological and/or physiological differences between NUN 3010 and Mata Hari (referred herein to as further distinguishing characteristics), in one, two, or all three of which NUN 3010 differs from Mata Hari when grown under the same environmental conditions, are:

6) Bulb skin color (USDA descriptor 6. BULB); Both bulbs of NUN3010 and Mata Hari have a Purplish Red skin color, but the color shade is different. NUN3010 bulbs have a noticeably different skin color; the bulbs of NUN3010 have a lighter "rosier" bulb skin color than MATA HARI (for example, skin color for NUN 3010 is RHS 59B, that of MATA HARI is RHS N77A);

7) bulb interior color (USDA descriptor 6. BULB); Both the bulbs of NU3010 and Mata Hari have a Purplish Red interior color, but the color shade of NUN3010 is different. NUN3010 bulbs have a different interior color than Mata Hari bulbs, for example, NUN 3010's interior color is RHS 77A, while the bulb interior color of MATA HARI is RHS 79A;

8) average days to maturity (USDA Descriptor 1. TYPE). days to maturity for NUN 3010 are significantly less compared to days to maturity of MATA HARI (for example, NUN 3010: 155 days; MATA HARI: 165 days)

Thus, an onion plant "comprising the distinguishing characteristics of NUN 3010", refers herein to a onion plant which does not differ significantly from NUN 3010 in characteristics 1) to 5) above. In a further aspect the onion plant further does not differ significantly from NUN 3010 in at least one, two or all three characteristics selected from characteristics 6) to 8) above (also referred to as "further distinguishing characteristics").

Also NUN 3010 has a different bulb shape than bulbs of Mata Hari, with bulbs of NUN 3010 being more "top" shaped (USDA's Top Shape (Texas Grano 502; UPOV's Broad Obovate) and bulbs of MATA HARI being more "deep globe" (USDA's Deep Globe, UPOV's Rhombic);

In one aspect a short-day onion plant, *Allium cepa*, is provided, designated variety NUN3010, a representative sample of seed of said variety having been deposited under Accession Number 42662 .

In one aspect, the onion plant has all the morphological and physiological characteristics of NUN3010 as shown in Table 1 when grown under the same environmental conditions, i.e. it does not differ significantly in any of the physiological and/or morphological characteristics from NUN3010.

The morphological and/or physiological differences between NUN 3010 and other known varieties, such as Mata Hari can easily be established by growing NUN 3010 next to the other varieties (in the same field or greenhouse under the same environmental conditions), preferably in several locations which are suitable for short-day onion cultivation, and measuring morphological and/or physiological characteristics of a number of plants (e.g., to calculate an average value (of at least 5, preferably at least 10, 15, or even more, plants and/or plant parts which were grown under the same conditions) and to determine the variation range/uniformity within the variety). Differences between varieties can be determined throughout the growing period as long as the plants to be compared developed the parts of said plants which are compared with each other.

For example, trials can be carried out in the USA (e.g. in areas of 10° to 30° mean latitude) whereby e.g., growth (maturity) characteristics, plant characteristics (e.g. height, leaf length and width and color, column length), bulb characteristics size, shape, skin color, interior color, pungency, storage) and pest and/or disease resistance/susceptibility can be measured and directly compared.

The morphological and/or physiological characteristics may vary with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the RHS-Chart (see, e.g., world wide net: http://www.rhs.org.uk/Plants/RHS-Publications/RHS-colour-charts).

In one embodiment a onion plant is provided, designated NUN 3010, representative seeds of said onion hybrid having been deposited under accession number NCIMB 42662.

In another aspect, a short-day onion plant is provided, which (statistically significantly) differs from NUN 3010 in at least one morphological and/or physiological characteristics, but which does not differ from NUN 3010 in the following characteristics when grown under the same conditions: 1) bulb size, 2) bulb weight, 3) bulb height, 4) bulb diameter and 5) sheath length.

In a further aspect, a short-day onion plant is provided, which (statistically significantly) differs from NUN 3010 in at least one morphological and/or physiological characteristics, but which does not differ from NUN 3010 in the following characteristics when grown under the same conditions: 1) bulb size, 2) bulb weight, 3) bulb height, 4) bulb diameter and 5) sheath length and which further does not significantly differ from the plant designated NUN3010 in one or more of the following characteristics when grown under the same conditions: 6) Bulb skin color 7) bulb interior color, 8) days to maturity. Thus, an onion plant "comprising the distinguishing characteristics of NUN 3010", refers herein to an onion plant which does not differ significantly from NUN 3010 in characteristics 1) to 5) above. In a further aspect the onion plant further does not differ significantly from NUN 3010 in at least one, two or all three characteristics selected from characteristics 6) to 8) above (also referred to as "further distinguishing characteristics").

In one embodiment any of the onion plants have/are 1) a bulb size "large" (in the categories large, medium, small); 2) an average bulb weight (at maturity) of at least 200 g, preferably at least about 220 g, 230 g or 240 g; 3) an average bulb height (at maturity) of at least about 7 cm, preferably at least about 7.2 cm, 7.3 cm, 7.4 cm or 7.5 cm, 4) an average bulb diameter (at maturity) of at least about 7.5 cm, preferably at least about 7.8 cm, 8.0 cm, 8.3 cm, 8.4 cm, or 8.5 cm; 5) an average sheath length (column length) of less than 50 mm, less than 48 mm, less than 47 mm or less than 46 mm; and optionally one or more of the following characteristics: 6) a Purplish Red bulb skin color, which has a color code of RHS 59B; 7) Purplish Red interior bulb color which has a color code of RHS 77A; and 8) average days to maturity of less than 160 days, preferably about 152 days, 153 days, 154 days 155 days, 156 days or 157 days.

In a further embodiment a onion plant is provided, which (statistically significantly) differs from the onion plant designated NUN 3010, representative seeds of said onion plant hybrid having been deposited under accession number NCIMB 42662, in at least 1, 2, 3, 4, or 5 morphological and/or physiological characteristics when grown under the same environmental conditions, whereby the morphological and/or physiological characteristics are those of Table 1. The onion plant does, thus, not differ in a statistically significant way from NUN 3010 in any of the other morphological and/or physiological characteristics of Table 1 when grown under the same conditions.

In one embodiment an onion plant is provided, designated NUN 3010, which does not (statistically significantly) differ in any of the morphological and/or physiological characteristics of Table 1 from plants grown from seeds deposited under accession number NCIMB 42662 when grown under the same environmental conditions.

In one aspect, the above described onion plants are obtained from in vitro cell- or tissue cultures. As already mentioned, in vitro cell or tissue cultures are known in the art and can be used to either vegetatively reproduce the plant from which the cells or tissues were obtained or to identify and/or select phenotypic variants, and to regenerate such variants. Once selected, such selected variants can then in turn also be reproduced true to type using in vitro cell- or tissue culture.

Thus, in one aspect, a onion plant is provided which is clonally propagated (it is a vegetative reproduction) from NUN 3010 cells or tissue and which comprises all the distinguishing characteristics of NUN 3010 when grown under the same environmental conditions. In another aspect it further comprises one or more of the further distinguishing characteristics. In yet another aspect it comprises all morphological and/or physiological characteristics of NUN 3010 as given in Table 1. And in yet a further aspect it comprises all morphological and/or physiological characteristics of NUN 3010 as given in Table, except that it significantly differs from NUN 3010 in 1, 2, 3, 4, or 5 of the morphological and/or physiological characteristics of Table 1.

Also plant parts of the above onion plants are provided. In one aspect the plant parts are selected from the group consisting of: explants, cells, flower buds, protoplasts, callus, tissues, cuttings, shoots, stems, meristem, leaf, bulb parts, bulb scales, sheath, root, root tip, cotyledon, flower, pollen, ovule, embryo.

Further, bulbs produced by NUN 3010, or by a phenotypic variant of NUN 3010, are provided herein. The bulbs are distinguished from other bulbs by the fact that the average bulb characteristics of the distinguishing characteristics 1) to 5) (above) and optionally 6), 7) and/or 8) above, do not significantly differ from the bulb characteristics 1) to 5) (and optionally 6, 7 and/or 8) of NUN 3010, a representative number of seeds having been deposited under Accession number NCIMB 42662, when grown under the same conditions.

Plants and plant parts and bulbs of NUN 3010 are, in one aspect, obtainable by growing seeds of which a representative sample has been deposited under the Budapest Treaty with Accession Number NCIMB 42662. Plants and plant parts and bulbs of a phenotypic variant of NUN 3010 are, in one aspect, obtainable by in vitro cell- or tissue-culture of cells or tissues of NUN 3010 and selection/and or identification of a phenotypic variant (optionally after mutagenesis treatment) as described above.

Seeds

Also provided are seeds of onion variety NUN 3010, i.e. seeds from which the variety can be grown. A representative sample of said seeds (at least 2500 seeds) has been deposited under the Budapest Treaty with Accession Number NCIMB 42662.

In one embodiment, a plurality of NUN 3010 seeds are packaged into small and/or large containers (e.g., bags, cartons, cans, etc.). Seeds may be treated with one or more chemical compounds and/or biological control agents (e.g. to improved germination, insecticidal-, acaricidal-, nematicidal- or fungicidal-compounds or compositions, etc.) and/or seeds may be primed. Biological control agents are one or more microorganisms which protect the seed or seedling against pathogens. For example, strains of bacteria and/or fungi, such as bacteria of the species of *Streptomyces, Pseudomonas, Bacillus* and *Enterobacter* or fungi of the species *Phomopsis, Ectomycorrhizae, Trichoderma, Cladosporium* and *Gliocladium*.

Priming is a water-based process that is performed on seeds to increase uniformity of germination and emergence from the soil, and thus enhance vegetable stand establishment. Methods how to prime onion seeds are well known in the art, see WO2008/107097, describing different priming methods, such as hydro-priming (including drum-priming), osmopriming and solid-matrix priming, which can be used. The priming process may also be combined with the chemical compounds or compositions and/or biological control agent treatment, so seeds may e.g. be hydrated in a first step, dried in a second step and treated in a third step with one or more seed treatment compounds or compositions. Priming is also sometimes referred to as seed conditioning.

Hydropriming includes those techniques in which seeds are allowed to take up water for a short period or at low temperatures, mostly at ample water supply. These techniques are sometimes also referred to as soaking or steeping. With osmopriming, the seeds are exposed to an osmotic solution (see e.g. WO2008/107097).

With solid matrix priming (SMP), seeds are mixed with water and solid carriers. Examples of solid carriers are vermiculite and diatomaceous silica products. The water is taken up by the seeds as well as absorbed on the solid particle surfaces, which in this way control the water uptake of the seeds. In addition to using particle-like carriers, SMP can be carried out using, amongst others, moist towels, gunny bags, moist sand, sterilised compost or press mud as well.

So, in one aspect seeds of NUN 3010 are provided wherein said seeds are primed seeds and/or chemically and/or biologically treated seeds, comprising one or more chemical compounds or compositions and/or one or more biological control agents, selected from the group consisting of: a compound that improves germination, an insecticidal compound, an acaricidal compound, a nematicidal compound, and a fungicidal compound.

Plant and Parts of NUN 3010 or of a Phenotypic Variant of NUN 3010

The present invention provides plants, including seedlings, and plant parts designated NUN 3010, and selfings of NUN3010 and EDVs of NUN 3010, including phenotypic variants of NUN3010. The below thus equally applies to selfings and EDVs of NUN3010, even though only NUN3010 is mentioned.

In particular, the invention provides plants and plant parts, including seedlings and bulbs of NUN 3010 obtained from germinating and growing the seeds of NUN 3010, a representative sample of seeds having been deposited under Accession number NCIMB 42662.

Other plant parts obtained from germinating NUN 3010 are parts such as cuttings, cotyledons, stems, leaves, flowers, roots, bulbs or parts of any of these.

Also parts of the seed of NUN 3010 itself are provided herein, such as seed coat, embryo, or endosperm.

Thus, any developmental stage and any part of the plant grown from seeds of 3010, or any part of the seed of NUN 3010, are provided herein.

Also, any plant regenerated from said plant part, i.e. any vegetative or clonal propagation of NUN 3010 is encompassed herein. This includes onion seedlings or plants grown from in vitro cell cultures or tissue cultures of cells or tissues of NUN 3010.

Thus, vegetative propagations of NUN 3010 may be generated by germinating seeds of NUN 3010 and obtaining plant cells or tissues from the seedling or from the plants grown from said seeds, or by obtaining cells or tissues from the seeds of NUN 3010, and regenerating a plant from said cells or tissue.

In another aspect the vegetative propagation comprises all the physiological and/or morphological characteristics of NUN 3010 provided in Table 1, when grown under the same environmental conditions. In yet another aspect the vegetative propagation comprises all the physiological and/or morphological characteristics of NUN 3010 provided in Table 1, except for 1, 2, 3, 4, or 5 of those characteristics, when grown under the same environmental conditions.

Also provided are parts of the onion plants designated NUN 3010 such as cuttings, bulbs or bulb parts (scales or scale parts), (immature) flowers, pollen, ovaries, leaves, cotyledons, stems, roots, clonally propagated plants, root tips, seedlings, seeds, parts of the seed (seed coat, embryo, endosperm, embryo sac), stalks, shoots, cells, protoplasts, meristems, buds etc. of variety NUN 3010, or parts of any of these. Such parts may be vegetative cells or tissues, which include, without limitation cuttings, roots, stems, cells or protoplasts, leaves, cotyledons, bulb-scales, meristems and buds.

Moreover, there is provided a cell culture or tissue culture of onion variety NUN 3010 in which the cell- or tissue culture is derived from a tissue such as, for example and without limitation, flower buds, bulb-scales, leaves, embryos, cotyledon, mesocotyls, meristematic cells, roots, root tips, flowers, seeds or stems. For example, flower bud, bulb-scales (or scale parts), leaf-, or stem-cuttings may be used in tissue culture.

Also provided are onion plants regenerated from the above-described plant parts, or regenerated from the above-described cell or tissue cultures, said regenerated plant having at least the distinguishing characteristics of NUN 3010 when grown under the same conditions, optionally also one or more further distinguishing characteristics of NUN 3010. In another aspect the plants have all morphological and/or physiological characteristics of NUN 3010 measured in Table 1, or all except 1,2,3,4 or 5 of the characteristics measured for NUN 3010 in Table 1. In a further aspect, the plants have all the distinguishing characteristics of NUN3010, and optionally one, two or three further distinguishing characteristics. These plants can also be referred to as "vegetative propagations of NUN 3010" or "vegetative propagations of phenotypic variants of NUN 3010".

Also provided are harvested bulbs of NUN 3010 or of a vegetative propagation of NUN 3010 or of a phenotypic variant of NUN 3010 and packages comprising a plurality of such bulbs, especially mature, marketable bulbs.

As already mentioned, also phenotypic variants of NUN 3010 are encompassed herein. In one embodiment, NUN 3010 seeds or cells or tissues of NUN 3010 may be mutated (by e.g. irradiation, chemical mutagenesis, heat treatment, etc.) and mutated seeds or cells or plant parts or plants may be selected in order to change one or more characteristics of NUN 3010.

Also, NUN 3010 or a phenotypic variant of NUN 3010 may be transformed and regenerated, whereby one or more chimeric genes are introduced into the variety. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 3010 by transforming NUN 3010 or a phenotypic variant thereof with a transgene that confers the desired trait, wherein the transformed plant retains all the distinguishing characteristics, optionally also one or more or all further distinguishing characteristics of NUN 3010. In one embodiment the transformed plant retains essentially all the morphological and physiological characteristics of NUN 3010 or of the phenotypic variant of NUN 3010 and contains the desired trait. In one embodiment the transformed plant retains essentially all except 1, 2, 3, 4, or 5 of the morphological and physiological characteristics of NUN 3010 measured in Table 1, or of the phenotypic variant of NUN 3010, and contains the desired trait. In a further aspect, the plants have all the distinguishing characteristics of NUN3010, and optionally one, two or three further distinguishing characteristics, and the desired trait.

The invention also provides a method of producing plants of variety designated NUN 3010, or a part thereof, or a phenotypic variant of NUN 3010, or a part thereof, comprising vegetative propagation of a plant designated NUN 3010 or designated a phenotypic variant of NUN 3010. In one embodiment, said vegetative propagation comprises regenerating a whole plant from a part of variety designated NUN 3010 or designated a phenotypic variant of NUN 3010. In one embodiment, said part of a plant is a cutting, root, stem, cell, protoplast, leaf, meristem, bud, bulb-scale, cell, cell culture or a tissue culture.

The method for vegetative reproduction of NUN 3010 (or a phenotypic variant of NUN 3010) comprises the steps of:
a) Providing an explant of NUN 3010 (or of a phenotypic variant of NUN 3010),
b) Culturing said explant in an in vitro culture,
c) Providing a shooting and a rooting medium to said explants,
d) Allowing the plants to grow.

Explants may be any plant parts of NUN 3010 (or of a phenotypic variant of NUN 3010) which is regenerable into a whole plant, such as parts of cotyledons, shoot tips, embryos, mesocotyls, leaves, stalk, cells, protoplasts, callus, meristems, etc.

If plants are regenerated they may be transferred to soil.

The regenerated plants may be grown e.g. in the field to produced bulbs.

The regenerated plants have all the distinguishing characteristics of NUN 3010, optionally also 1, 2, or all 3 further distinguishing characteristics. In another embodiment the regenerated plants have essentially all, or all except 1, 2, 3, 4 or 5, of the physiological and/or morphological characteristics of NUN 3010.

In another aspect the invention provides a method for identifying and/or selecting a phenotypic variant of NUN 3010, said method comprises the steps of:
a) Providing an explant of NUN 3010,
b) Culturing said explant in an in vitro culture,
c) Providing a shooting and a rooting medium to said explants,
d) Allowing rooted plants to grow,
e) Identifying and/or selecting a phenotypic variant.

Explants may be any plant parts of NUN 3010 which is regenerable into a whole plant, such as parts of cotyledons, shoot tips, embryos, mesocotyls, leaves, stalk, cells, protoplasts, callus, meristems, etc.

Optionally, the explants may be treated with a mutagen, such as X-rays, UV-radiation, EMS or another chemical mutagen, to induce genotypic and phenotypic variation. As mentioned earlier, the phenotypic variant is preferably stable in the altered characteristics, i.e. the modified phenotypic characteristic(s) is/are also seen in the mature plant. The phenotypic variant may also be clonally propagated, to produce many plants of the phenotypic variant and to produce fruits on those plants.

In vitro propagation of onion can be carried as described Chapter 25 "Micropropagation of Onion (*Allium cepa L.*) from Immature Inflorescences" by Pablo Marinangeli, in the book "Protocols for Micropropagation of Selected Economically-Important Horticultural Plants" (Editors: Maurizio Lambardi, Elif Aylin Ozudogru, Shri Mohan Jain, ISBN: 978-1-62703-073-1). Herein different media are described which can be suitably used as shooting/shoot elongation or rooting media.

In another aspect the invention provides a method for identifying and/or selecting a phenotypic variant of NUN 3010, said method comprises the steps of:
 a) Providing a plurality of seeds of NUN 3010,
 b) Optionally treating said seeds with a mutagenic agent,
 c) Allowing the seeds to germinate and grow,
 d) Identifying and/or selecting a phenotypic variant of NUN 3010.

Also in this method the phenotypic variant is preferably stable in the altered characteristics, i.e. the modified phenotypic characteristic(s) is/are also seen in the mature plant. The phenotypic variant may also be clonally propagated, to produce many plants of the phenotypic variant and to produce fruits on those plants.

Thus, a vegetative propagated plant (or a part thereof) is provided having the distinguishing characteristics of NUN 3010; optionally having one or more of the further distinguishing characteristics of NUN 3010. In one embodiment the vegetative propagated plant has all the essential morphological and physiological characteristics of the watermelon plant designated NUN 3010 when grown under the same environmental conditions. In some embodiments, said propagated plant differs from NUN 3010 in 1, 2, 3, 4, or 5 of the characteristics of Table 1, but otherwise has all the essential and/or morphological characteristics of NUN 3010 when grown under the same conditions. In one aspect the plant does not differ from NUN3010 in the distinguishing characteristics 1) to 5) and optionally also not in one or more of the further distinguishing characteristics 6), 7) and 8).

When referring to the morphological and/or physiological characteristics of Table 1, or as described or measured in Table 1, it is understood that the characteristics named under the heading USDA Descriptor are referred to.

The invention also provides for a method of producing a vegetatively propagated plant of variety designated NUN 3010, or a part thereof, comprising regeneration of said plant from a cell culture or a tissue culture. Also provided are plants which are regenerated from such a cell culture or tissue culture.

As described above, the invention also relates to a phenotypic variant of NUN 3010 and a method for producing such as variant. The phenotypic variant differs from NUN 3010 in one or more or a few morphological and/or physiological characteristics, but is still genetically closely related to NUN 3010. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 3010 if its DNA fingerprint is at least 80%, 90%, 95%, 97% or 98% identical to the fingerprint of NUN 3010. In a preferred embodiment amplified fragment length polymorphism (AFLP) markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (van Eeuwijk and Law (2004), Euphytica 137: 129-137). In one embodiment a closely related plant of NUN 30107 has a Jaccard Similarity index of higher than 0.96.

Breeding of Onion Plants of the Invention

One aspect of the current invention concerns methods for crossing an onion variety provided herein with itself or a second plant and the seeds and plants produced by such methods. These methods can be used for propagation of a variety provided herein, or can be used to produce hybrid onion seeds and the plants grown therefrom. Such hybrid seeds can be produced by crossing the parent varieties of the variety.

The development of new varieties using one or more starting varieties is well known in the art. In accordance with the invention, novel varieties may be created by crossing a plant of the invention followed by multiple generations of breeding according to such well known methods. New varieties may be created by crossing with any second plant. In selecting such a second plant to cross for the purpose of developing novel varieties, it may be desired to choose those plants that either themselves exhibit one or more selected desirable characteristics or that exhibit the desired characteristic(s) when in hybrid combination. Once initial crosses have been made, inbreeding and selection take place to produce new varieties. For development of a uniform variety, often five or more generations of selfing and selection are involved.

Uniform varieties of new varieties may also be developed by way of double-haploids. This technique allows the creation of true breeding varieties without the need for multiple generations of selfing and selection. In this manner, true breeding varieties can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous variety.

Backcrossing can also be used to improve an inbred plant. Backcrossing transfers one or more heritable traits from one inbred or non-inbred source to an inbred that lacks those traits. The exact backcrossing protocol will depend on the characteristic(s) or trait(s) being altered to determine an appropriate testing protocol. When the term variety NUN 3010 is used in the context of the present invention, this also includes plants modified to include at least a first desired heritable trait such as one, two or three desired heritable trait(s).

This can be accomplished, for example, by first crossing a superior inbred (recurrent parent) to a donor inbred (non-recurrent parent), which carries the appropriate genetic information (e.g., an allele) at the locus or loci relevant to the trait in question. The progeny of this cross are then mated back to the recurrent parent followed by selection in the resultant progeny (first backcross generation, or BC1) for the desired trait to be transferred from the non-recurrent parent. After five or more backcross generations with selection for the desired trait, the progeny are heterozygous at loci controlling the characteristic being transferred, but are like the superior parent for most or almost all other loci. The last backcross generation would be selfed to give pure breeding progeny for the trait being transferred.

The parental onion plant which contributes the desired characteristic or characteristics is termed the non-recurrent parent because it can be used one time in the backcross protocol and therefore need not recur. The parental onion plant to which the locus or loci from the non-recurrent parent are transferred is known as the recurrent parent as it is used for several rounds in the backcrossing protocol.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection or screening may be applied where the single locus (e.g. allele) acts in a dominant fashion. For example, when selecting for a dominant allele providing resistance to a bacterial disease, the progeny of the initial cross can be inoculated with bacteria prior to the backcrossing. The inoculation then eliminates those plants which do not have the resistance, and only those plants which have the resistance allele are used in the subsequent backcross. This process is then repeated for all additional backcross generations.

Although backcrossing methods are simplified when the characteristic being transferred is a dominant allele, recessive, co-dominant and quantitative alleles may also be transferred. In this instance, it may be necessary to introduce a test of the progeny to determine if the desired locus has been successfully transferred. In the case where the non-recurrent variety was not homozygous, the F1 progeny would not be equivalent. F1 plants having the desired genotype at the locus of interest could be phenotypically selected if the corresponding trait was phenotypically detectable in a heterozygous or hemizygous state. In the case where a recessive allele is to be transferred and the corresponding trait is not phenotypically detectable in the heterozygous of hemizygous state, the resultant progeny can be selfed, or crossed back to the donor to create a segregating population for selection purposes. Non-phenotypic tests may also be employed. Selected progeny from the segregating population can then be crossed to the recurrent parent to make the first backcross generation (BC1).

Molecular markers may also be used to aid in the identification of the plants containing both a desired trait and having recovered a high percentage of the recurrent parent's genetic complement. Selection of onion plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay that is able to identify the relative presence or absence of a trait of interest in a plant can also be useful for breeding purposes. Procedures for marker assisted selection applicable to the breeding of onion are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs), Simple Sequence Repeats (SSR), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs), and Single Nucleotide Polymorphisms (SNPs).

Onion varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

The varieties and varieties of the present invention are particularly well suited for the development of new varieties or varieties based on the elite nature of the genetic background of the variety. In selecting a second plant to cross with NUN 3010 for the purpose of developing novel onion varieties, it will typically be preferred to choose those plants that either themselves exhibit one or more selected desirable characteristics or that exhibit the desired characteristic(s) when in hybrid combination. Examples of desirable characteristics may include, but are not limited to herbicide tolerance, pathogen resistance (e.g., insect resistance, nematode resistance, resistance to bacterial, fungal, and viral disease), male fertility, improved harvest characteristics, enhanced nutritional quality, increased antioxidant content, improved processing characteristics, high yield, improved characteristics related to the bulb flavor, texture, size, shape, durability, shelf life, and yield, increased soluble solids content, uniform ripening, delayed or early ripening, adaptability for soil conditions, and adaptability for climate conditions. Of course, certain traits, such as disease and pest resistance, and high yield are of interest in any type of onion variety or variety.

Plants of the Invention Derived by Genetic Engineering

Many useful traits that can be introduced by backcrossing, as well as directly into a plant, are those that are introduced by genetic transformation techniques. Genetic transformation may therefore be used to insert a selected transgene into the onion variety of the invention or may, alternatively, be used for the preparation of varieties containing transgenes that can be subsequently transferred to the variety of interest by crossing. Methods for the transformation of plants, including onion, are well known to those of skill in the art. Techniques which may be employed for the genetic transformation of onion include, but are not limited to, electroporation, microprojectile bombardment, *Agrobacterium*-mediated transformation, pollen-mediated transformation, and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

To effect pollen-mediated transformation, one may apply pollen pretreated with DNA to the female reproduction parts of onion plants for pollination. A pollen-mediated method for the transformation of onion is disclosed in U.S. Pat. No. 6,806,399.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the microprojectile stopping plate.

An illustrative embodiment of a method for delivering DNA into plant cells by acceleration is the BIOLISTICS Particle Delivery System, which can be used to propel particles coated with DNA or cells through a screen, such as a stainless steel or Nytex screen, onto a surface covered with target onion cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant species where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (see, e.g., U.S. Pat. No. 5,563,055).

Transformation of plant protoplasts also can be achieved using methods based on calcium phosphate precipitation, polyethylene glycol treatment, electroporation, and combinations of these treatments which are well known in the art. Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for onion plant gene expression include, but are not limited to, the cauliflower mosaic virus (CaMV) P-35S promoter, which confers constitutive, high-level expression in most plant tissues, including monocots; a tandemly, partially duplicated version of the CaMV 35S promoter, the enhanced 35S promoter (P-e35S) the nopaline synthase promoter, the octopine synthase promoter; and the figwort mosaic virus (P-FMV) promoter (see, e.g., U.S. Pat. No. 5,378,619) and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter; maize rbcS promoter; or chlorophyll a/b-binding protein promoter), (3) hormones, such as abscisic acid, (4) wounding; or (5) chemicals such as methyl jasmonate, salicylic acid, or Safener. It may also be advantageous to employ organ-specific promoters.

Exemplary nucleic acids which may be introduced to the onion varieties of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into an onion plant according to the invention. Non-limiting examples of particular genes and corresponding phenotypes one may choose to introduce into an onion plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. No. 5,500,365 and U.S. Pat. No. 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (e.g., a ribozyme) engineered to cleave a desired endogenous mRNA product. Thus, any gene which produces a protein or mRNA which expresses a phenotype or morphology change of interest is useful for the practice of the present invention.

DEPOSIT INFORMATION

A total of 2500 seeds of the hybrid variety NUN 3010 were deposited according to the Budapest Treaty by Nunhems B.V. on Sep. 20, 2016, NCIMB Ltd., Ferguson Building, Craibstone Estate, Bucksburn, Aberdeen AB21.9YA, United Kingdom (NCIMB). The deposit has been assigned Accession Number NCIMB 42662.

A deposit of NUN 3010 and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Although the foregoing invention has been described in some detail by way of illustration and example for purposes of clarity and understanding, it will be obvious that certain changes and modifications may be practiced within the scope of the invention, as limited only by the scope of the appended claims.

EXAMPLES

Development of NUN 3010 ON

The hybrid NUN 3010 was made from male and female proprietary inbred lines developed by Nunhems. The female parent of NUN 3010 and its maintainer was developed out of an internal breeding line. This inbred was developed over a period of 12 years/7 generations of inbreeding using single bulb selfing.

The male parent was developed from a [fertile×fertile] cross of two Nunhems inbred lines over a period of 8 generations of single bulb selfings.

The female and male parents were crossed to produce hybrid (F1) seeds of NUN 3010. The seeds of NUN 3010 can be grown to produce hybrid plants and parts thereof (e.g. onion bulbs). The hybrid NUN 3010 can be propagated by seeds or vegetative.

The hybrid variety is uniform and genetically stable. This has been established through evaluation of horticultural characteristics. Several hybrid seed production events resulted in no observable deviation in genetic stability. NUN 3010 has been observed for more than three generations in different trials on different locations and during seed increase.

Coupled with the confirmation of genetic stability of the female and male parents the Applicant concluded that NUN 3010 is uniform and stable.

MATA HARI is considered to be the most similar variety to NUN 3010. MATA HARI is a commercial variety from Nunhems. In Table 1 a comparison between NUN 3010 and MATA HARI is shown based on a trial in the USA. Trial location: Bakersfield, near Lamont, Calif., USA (coordinates: 35°13'54" N, 118°54'12" W). Transplanting date: Nov. 18, 2011.

Two replications of 50 plants each, from which 20 plants or plant parts were randomly selected, were used to measure characteristics. In Table 1 the USDA descriptors of NUN 3010 (this application) and reference MATA HARI (commercial variety) are listed.

In accordance with one aspect of the present invention, there is provided a plant having the physiological and morphological characteristics of onion variety NUN 3010. A description of the physiological and morphological characteristics of onion variety NUN 3010 is presented in Table 1.

TABLE 1

| Comparison between values* of NUN 3010 and MATA HARI | | |
|---|---|---|
| USDA Descriptor | Application Variety NUN 3010* | Comparison Variety MATA HARI* |
| 1. TYPE: | | |
| 1 = Bulb 2 = Bunching | 1 | 1 |
| 1 = short day; 2 = long day | 1 | 1 |
| Adaptation range Degree mean latitude | 10°-35° | 25°-35° |
| Maturity (days) 1 = early (75-90); 2 = medium (100-120); 3 = late (>130) | 3 (e.g., 155 days) | 3 (e.g., 165 days) |
| 2. PLANT: | | |
| Height above soil line to highest point of any foliage | 63.3 cm | 63.8 cm |
| 1 = erected (Spartam Gem); 2 = intermediate; 3 = floppy (Epoch) | 1 | |
| 3. LEAF: | | |
| Length (before maturity yellowing begins) | 41.7 cm | 48.2 cm |
| Width | 23.5 mm | 20.1 mm |
| Thickness (at mid-length of longest leaf) | 1.7 mm | 1.6 mm |

TABLE 1-continued

Comparison between values* of NUN 3010 and MATA HARI

| USDA Descriptor | Application Variety NUN 3010* | Comparison Variety MATA HARI* |
|---|---|---|
| Color: | 2 | |
| 1 = light green (Early Grano); | | |
| 2 = medium green (Yellow Bermuda); | | |
| 3 = blue green (Australian Brown U.C. No. 1) | | |
| Color Chart Name | RHS | RHS |
| Color Chart Code | 137A | |
| Bloom: | 2 | |
| 1 = none-glossy; | | |
| 2 = light (Early Grano); | | |
| 3 = medium (Crystal Wax); | | |
| 4 = heavy (California Early Red) | | |
| 4. SHEATH: | | |
| Column length (height from soil line to base of lowest succulent leaf) | 45.2 mm | 59.7 mm |
| Diameter (at mid-length) | — | — |
| Scape (from soil line to base of inflorescence) | — | — |
| Scape (diameter at mid-length) | — | — |
| 5. INFLORESCENCE: | | |
| Maximum No. per plant | — | — |
| Minimum No. per plant | — | — |
| Average No. per plant | — | — |
| Diameter | — | — |
| 1 = compact; 2 = loose/open; 3 = shaggy | | |
| Spathe 1 = long beak; 2 = short beak | — | — |
| Flower color: 1 = white; 2 = green; 3 = bright green | — | — |
| Anther length | — | — |
| Anther color | — | — |
| 1 = light green; | | |
| 2 = dark green; | | |
| 3 = yellow; | | |
| 4 = pale yellow; | | |
| 5 = chocolate; | | |
| 6 = red | | |
| Pollen viability 1 = sterile; 2 = fertile | — | — |
| Sepal Shape 1 = long pointed; 2 = round short | — | — |
| 6. BULB: | | |
| Size (harvested) | 3 | 2 |
| 1 = small (Red Creol); | | |
| 2 = medium (Australian Brown U.C. No. 1); | | |
| 3 = large (Early Grano) | | |
| Shape | 4 | 2 |
| 1 = Globe (White Sweet Spanish) | (Broad Obovate)*** | (Rhombic)*** |
| 2 = Deep Globe (Abundance) | | |
| 3 = Flt. Globe (Australian Brn. U.C. No. 1) | | |
| 4 = Top Shape (Texas Grano 502) | | |
| 5 = Deep Flat (Granex) | | |
| 6 = Thick Flat (Ebenezer) | | |
| 7 = Flat (Crystal Wax) | | |
| 8 = Torpedo-Long Oval (Italian Red) | | |
| Height | 7.5 cm | 6.8 cm |
| Diameter | 8.5 cm | 7.3 cm |
| Shape Index | 0.9 | 0.9 |
| 1 = invaginate; 2 = evaginate | 2 | 2 |
| Color (skin): | 2 | 2 |
| 01 = Brown (Australian Brn. U.C. No. 1) | RHS 59B | RHS N77A |
| 02 = Purplish Red (Italian Red) | | |
| 03 = Buff Red (Red Creole) | | |
| 04 = Pinkish Yellow (Ebenezer) | | |
| 05 = Brownish Yellow (Mt. Danvers) | | |
| 06 = Deep Yellow (Brigham Yellow Globe) | | |
| 07 = Medium Yellow (Early Yellow Globe) | | |
| 08 = Pale Yellow (Yellow Bermuda) | | |
| 09 = White (White Sweet Spanish) | | |
| 10 = Other (Specify) _____ | | |
| Color (interior) | 3 | 3 |
| 1 = Pink; 2 = Red; 3 = Purplish Red; 4 = White; | RHS 77A | RHS 79A |
| 5 = Cream; 6 = Light Green-Yellow; 7 = Dark Green-Yellow | | |

TABLE 1-continued

Comparison between values* of NUN 3010 and MATA HARI

| USDA Descriptor | Application Variety NUN 3010* | Comparison Variety MATA HARI* |
|---|---|---|
| Weight** | 242.7 g | 191.3 g |
| Scales: | 1 | 1 |
| 1 = Few (Crystal Wax) | | |
| 2 = Medium (Australian Brown U.C. No. 1) | | |
| 3 = Many (Sweet Spanish) | | |
| Scales: | 2 | 2 |
| 1 = Thick (Australian Brown U.C. No. 1) | | |
| 2 = Medium (Red Creole) | | |
| 3 = Thin (Crystal Wax) | | |
| Scale retention: | 3 | 3 |
| 1 = Very Good (Australian Brn. U.S. No. 1) | | |
| 2 = Good (Ebenezer) | | |
| 3 = Fair (Red Wethersfield) | | |
| 4 = Poor (Crystal Wax) | | |
| Pugence: | 2 | 2 |
| 1 = Mild (Early Grano) | | |
| 2 = Medium (Crystal Wax) | | |
| 3 = Strong (White Creole) | | |
| Storage: | 3 | 3 |
| 1 = Good (Ebenezer) | | |
| 2 = Fair (Yellow Globe Danvers) | | |
| 3 = Poor (Crystal Wax) | | |

*These are typical values. Values may vary due to environment. Other values that are substantially equivalent are also within the scope of the invention.
**No USDA descriptor
***UPOV descriptor As described above, variety NUN 3010 exhibits desirable agronomic traits, including a sheath length which is at least 15%, 20% or 25% shorter than that of MATA HARI; a larger bulb size and bulb weight as compared to MATA HARI which is shown by an at least 5% or 10% larger bulb height, an at least 10% or 15% larger bulb diameter, and an at least 15%, 20% or 25% higher bulb weight.

In a further embodiment, days to maturity for NUN 3010 are less compared to days to maturity of MATA HARI (for example, NUN 3010: 155 days; MATA HARI: 165 days), a bulb NUN 3010 can be distinguished from a bulb of MATA HARI by its shape (for example, the bulb shape of bulbs of NUN 3010 is more "top" shaped (USDA's Top Shaper (Texas Grano 502); UPOV's Broad Obovate) while MATA HARI is more "deep globe" (USDA's Deep Globe, UPOV's Rhombic); a noticeably lighter "rosier" bulb skin color than MATA HARI (skin color for NUN 3010 is RHS 59B, that of MATA HARI RHS N77A); a different bulb interior color: NUN 3010's interior color is RHS 77A, MATA HARI's RHS 79A; and NUN 3010 is resistant to Onion Pink Root (*Phoma* (*Pyrenochaeta*) *terrestris*).

All references cited herein are hereby expressly incorporated herein by reference.

REFERENCES

The following references, to the extent that they provide exemplary procedural or other details supplementary to those set forth herein, are specifically incorporated herein by reference:
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 5,378,619
U.S. Pat. No. 6,806,399
WO 99/31248
EP 0 534 858
Choi et al., Plant Cell Rep., 13: 344-348, 1994.
Ellul et al., Theor. Appl. Genet., 107:462-469, 2003.

What is claimed is:

1. An onion plant of variety NUN 3010, a representative sample of seed of said variety having been deposited under ATCC Accession Number 42662.

2. A seed of variety NUN 3010, a representative sample of seed of said variety having been deposited under ATCC Accession Number 42662.

3. A plant part of the plant of claim 1 wherein said plant part comprises the same genetic makeup as the plant of claim 1.

4. The plant part of claim 3, further defined as a leaf, pollen, cutting, flower, pollen, meristem, bud, root, root tip, an ovule, a bulb, bulb-scales, or a cell.

5. The plant part of claim 3, further defined as a bulb.

6. An onion plant, or a part thereof, which has all the physiological and morphological characteristics of Table 1 of the plant of claim 1 when grown under the same conditions.

7. A tissue culture of regenerable cells of the plant of claim 1.

8. The tissue culture according to claim 7, comprising cells or protoplasts from a plant part selected from the group consisting of embryos, meristems, cotyledons, pollen, leaves, anthers, roots, root tips, pistil, flower, seed and bulbs.

9. An onion plant regenerated from the tissue culture of claim 7, comprising all the physiological and morphological characteristics of the plant of claim 1 as provided in Table 1.

10. A method of vegetatively propagating the plant of claim 1 comprising the steps of:
    (a) collecting tissue capable of being propagated from a plant according to claim 1;

(b) cultivating said tissue to obtain proliferated shoots; and
(c) rooting said proliferated shoots to obtain rooted plantlets.

11. The method of claim 10, further comprising growing plants from said rooted plantlets.

12. A method of producing an onion plant, said method comprising crossing the plant of claim 1 with a second onion plant one or more times, and selecting progeny from said crossing.

13. A method of introducing a desired trait into an onion variety comprising:
(a) crossing a plant of variety NUN 3010, a representative sample of seed of said variety having been deposited under ATCC Accession Number 42662 with a second onion plant that comprises a desired trait to produce F1 progeny;
(b) selecting an F1 progeny that comprises the desired trait;
(c) optionally selfing the F1 progeny one or more times to produce F2, F3 or further generation selfing progeny;
(d) crossing the selected F1 progeny or the selfing progeny with a plant of variety NUN 3010 to produce backcross progeny;
(e) selecting backcross progeny comprising the desired trait and essentially all the physiological and morphological characteristic of onion variety NUN 3010; and optionally
(f) repeating steps (d) and (e) one or more times in succession to produce selected fourth or higher backcross progeny that comprise the desired trait.

14. A method of producing a plant comprising an added desired trait, the method comprising introducing a transgene conferring the desired trait into a plant of onion variety NUN 3010.

15. A method for producing a seed of a variety derived from NUN 3010 comprising the steps of:
(a) crossing an onion plant of variety NUN 3010 with a second onion plant; and
(b) allowing seed of a variety NUN 3010-derived onion plant to form.

16. The method of claim 14 further comprising the steps of:
(c) crossing a plant grown from said variety NUN 3010-derived onion seed with itself or a second onion plant to yield additional variety NUN 3010-derived onion seed;
(d) growing said additional variety NUN 3010-derived onion seed of step (c) to yield additional variety NUN 3010-derived onion plants; and optionally
(e) repeating the crossing and growing steps of (c) and (d) to generate further variety NUN 3010-derived onion plants.

17. The method of claim 14, wherein the second onion plant is of an inbred onion variety.

18. A method of producing an onion bulb comprising:
(a) obtaining a plant according to claim 1, wherein the plant has been cultivated to maturity; and
(b) collecting a bulb from said plant.

19. A food or feed product comprising a bulb or a bulb-part of the plant of claim 1.

* * * * *